United States Patent [19]

Scharf et al.

[11] Patent Number: 5,620,569
[45] Date of Patent: Apr. 15, 1997

[54] PROCESS FOR THE PHOTOOXIDATION OF TERPENE OLEFINS

[75] Inventors: Hans-Dieter Scharf, Roetgen; Peter Esser; Walter Kuhn, both of Holzminden; Ralf Pelzer, Fürstenberg, all of Germany

[73] Assignee: Haarmann & Reimer GmbH, Holzminden, Germany

[21] Appl. No.: 358,129

[22] Filed: Dec. 16, 1994

[30] Foreign Application Priority Data

Dec. 23, 1993 [DE] Germany .................. 43 44 163.7

[51] Int. Cl.$^6$ .............. C07F 1/00; C07C 29/00; C07C 401/00; C07C 41/00
[52] U.S. Cl. ................. 204/157.6; 204/157.61; 204/157.9; 204/157.91; 204/157.92
[58] Field of Search ............ 204/157.9, 157.91, 204/157.92, 157.6, 157.61

[56] References Cited

U.S. PATENT DOCUMENTS 3,382,276  5/1968  Schenck et al. ............. 204/157.9
3,505,412  4/1970  Klein ...................... 260/631.5

FOREIGN PATENT DOCUMENTS 55-28965  2/1980  Japan.
55-55126  4/1980  Japan.

OTHER PUBLICATIONS

Patel et al., "Synthetic Studies on Roseoxide", Indian J. of Chem., vol. 16B, No. 3, pp. 188–190. March 1978.
Chemical Abstracts of Japan, vol. 5, No. 140, Abstract of JP 56-75472 (June 1981).
O. Schenck, et al., Chem. Ind. (london) No. 10, p. 459 (March 1962).
Patent Abstracts of Japan, vol. 4, No. 61, Abstract of JP 55-28965 Feb. 1980).
Chemical Abstracts, 98: 215833h (Dec. 1982).

*Primary Examiner*—Kathryn Gorgos
*Assistant Examiner*—Edna Wonz
*Attorney, Agent, or Firm*—Sprung Horn Kramer & Woods

[57] ABSTRACT

In the photooxidation of terpene olefins, fewer by-products and higher conversion rates are obtained if a very high irradiation intensity is chosen.

14 Claims, No Drawings

PROCESS FOR THE PHOTOOXIDATION OF TERPENE OLEFINS

The invention relates to a process for the oxidation of olefinic terpenes with oxygen under sunlight or artificial light of high irradiance.

The oxidation of olefinic terpenes with oxygen under the action of light in the presence of a sensitizer represents a useful method for the preparation of peroxides and hydroperoxides which are valuable intermediates for the preparation of aroma substances.

Thus, for example, α- and β-pinene (DE-C 933 925 and G. O. Schenck et al., Liebigs Ann. Chem. 584, 177 (1953)), β-citronellol (G.Ohloff et al., Angew. Chem. 73, (1961)), 3-carene (G. O. Schenck et al., Chem. and Ind. 1962, 459), α-thujene (E. Klein et al., Chem. Ber. 98, 3045 (1965)), terpinolene (DE-B 12 35 306) and nerol (G.Ohloff et al., Helv. Chim. Acta 47, 602 (1964)) have already been photooxidized. The authors have sometimes used sunlight, sometimes artificial light; in many cases the yield was unsatisfactory, but regularly the yield was inadequate with respect to the reaction time.

It has now surprisingly been found that fewer by-products and higher conversion rates are obtained if a very high irradiation intensity is chosen.

The invention therefore relates to a process for the oxidation of olefinic terpenes with oxygen under the influence of light, characterized in that the irradiation intensity is chosen so that the reaction achieves a conversion rate of 95% in less than 12 hours.

Such a conversion rate is generally achieved at an irradiation intensity of 5 to 200 suns, preferably 10 to 100 suns.

It has further been found that the reaction proceeds with a particularly good result if UV light is to a very high degree excluded, i.e. no more than 10% of the total energy of the light emitted is apportioned to the wavelength range from 200 to 400 nm and preferably no more than 1% of the total energy of the light emitted is apportioned to the wavelength range from 200 to 300 nm—in each case based on the wavelength range from 200 to 700 nm radiated from the light source.

Olefinic terpenes preferred for the process according to the invention include, for example, acyclic olefinic terpenes with or without hydroxyl groups, such as myrcene, ocimene, geraniol, nerol, linalool, myrcenol, lavandulol, citronellol, monocyclic olefinic terpenes such as limonene, α- and γ-terpinene, terpinolene, α- and β-phellandrene and bicyclic olefinic terpenes such as α- and β-pinene, camphene, carene and α-thujene.

The reaction can be carried out in an organic solvent inert under reaction conditions. These solvents should adequately dissolve the starting material and end product and the sensitizer and positively influence the life of singulet oxygen. Such solvents include, for example, aliphatic and cycloaliphatic hydrocarbons such as benzine and cyclohexane, chlorinated aliphatic hydrocarbons such as dichloromethane, chloroform and tetrachloromethane, highly fluorinated hydrocarbons such as hexafluorobenzene, polyfluoroheptane, aromatic hydrocarbons such as benzene, toluene and xylenes, chlorinated aromatic hydrocarbons such as chlorobenzene, monohydric and dihydric aliphatic alcohols such as methanol, ethanol, n-propanol, isopropanol, n- and tert-butanol, ethylene glycol, ethers such as diethyl ether and dibutyl ether, tetrahydrofuran and dioxane, $C_1$–$C_6$ alkyl esters of $C_2$–$C_4$ carboxylic acids, such as ethyl and butyl acetates, ethers and esters of ethylene glycol and propylene glycol such as ethylene glycol monomethyl ether and ethylene glycol monoethyl ether, ethylene glycol monomethyl ether acetate, ethylene glycol monoethyl ether acetate and propylene glycol diacetate, ketones such as acetone, methyl ethyl ketone and cyclohexanone, $C_1$–$C_6$ carboxylic acids such as acetic acid, amides such as dimethylformamide, dimethylacetamide, sulfolane, N-methylpyrrolidone and N-methylcaprolactam, and nitriles such as acetonitrile. Aliphatic $C_1$–$C_6$ alcohols are particularly preferred.

Preferred sensitizers include xanthene pigments such as fluorescein, eosine, erythrosine B and Rose Bengal, phenothiazine pigments such as methylene blue and porhyrins or porphins such as tetraphenylporhyrin, zinc tetraphenylporhin and chlorophyll. The concentration of sensitizer chosen depends essentially upon the path length of the irradiated solution at the irradiation window it is generally 100 ppm to 5% by weight, based on irradiated solution. It may be advantageous to add part of the sensitizer in the course of the reaction.

For the oxidation, pure oxygen or oxygen-containing gases such as air can be used. Gas addition is carried out at the position of highest pressure the amount depends on the solubility in the selected solvent at reaction temperature. Mixing with the solvent can be carried out in a conventional manner, e.g. using a static mixer. In order to be able to employ a high oxygen concentration, the reaction can also be carried out under pressure (preferably up to 10 bar).

The reactor systems to be used include, in addition to gas metering, a light concentration system, a vessel having an irradiation window, a transport apparatus for the reaction solution (preferably a pump apparatus) and if required a cooling apparatus.

Examples of light concentration systems which are particularly suitable are parabolic mirrors, for example in the form of parabolic mirror channels, and heliostat fields or parabolic dishes. The shape of the irradiation windows depends expediently on the type of the light concentration system used; for example when a parabolic mirror channel is used, the reactor which will be used is a glass tube concentrated in the focal line of this mirror channel. The absorption of thermal energy can be restricted, for example, by enabling the passage through the reactor of non-absorbed radiation or preventing rays having wavelengths above the threshold wavelength of the photochemical reaction from passing into the reaction solution at all by using a dividing mirror which reflects long-wave light but permits the passage of short-wave light.

According to a preferred embodiment, the sun is utilized as light source. The degree of concentration achieved by the light concentration system is shown as an increase of the irradiation intensity at the irradiation window of the photoreactor in relation to the direct solar irradiation. This is determined by means of pyrheliometers, a method standardized by the World Radiation Centre in Davos/Switzerland.

When artificial light is used, e.g. undoped high-pressure mercury vapour lamps, xenon lamps, preferably thallium iodide-doped high-pressure mercury vapour lamps and low-pressure sodium lamps are suitable. According to a preferred embodiment, the lamps are arranged in parallel around an absorber tube.

Determination of the proportion of the total irradiated energy apportioned to the wavelength range from 200 to 400 nm or 200 to 300 nm is best performed by a differential measurement, according to which the total energy (TE) emitted up to 700 nm is first determined and then, using additional suitable filters, the partial energy (PE) of the light source emitted between 400 and 700 nm or between 300 and 700 nm is determined; the difference $$100 - \frac{TE - PE}{TE}$$

then gives the percentage proportion of the radiation energy between 200 and 400 nm or between 300 and 400 um.

The volume of the reactor parts furnished with irradiation window as a proportion of total volume of the reactor principally depends on safety concerns and is generally 5 to 50, preferably 7 to 30%.

The reaction is preferably carried out at temperatures of 0° to 60° C., in particular 10° to 40° C.

The photooxidation products prepared by the process according to the invention represent valuable intermediates for the aroma substance industry. Because of their hydroperoxide groups, work-up of the reaction mixture is often dispensed with and further processing of the product is generally preferred. Thus, the hydroperoxides can, for example, be converted with conventional reducing agents, e.g. as described in "Methoden der Organischen Chemie" [Methods in Organic Chemistry] (Houben-Weyl), 4th edition Vol. 4/1d, p. 456, Georg Thieme Verlag, Stuttgart-New York 1981, and in the literature references cited there, into the corresponding alcohols. Preferred reducing agents include, e.g., hydrogen in the presence of conventional hydrogenation catalysts, e.g. Raney nickel or palladium on activated carbon, alkali metal aluminium hydrides such as lithium aluminium hydride and sodium aluminium hydride, triphenylphosphine and, in particular, sodium sulphite, preferably in aqueous solution. The resulting hydroxyterpene can then be used as such or in the form of its secondary products as an aroma substance.

Thus, for example, the hydroperoxide resulting from citronellol can be reduced to the hydroxyl compound, whereupon a ring closure can follow, e.g. in the presence of sulphuric acid, to give rose oxide.

The hydroperoxide resulting from α-thujene can be reduced to 4-hydroxy-β-thujene and can then be hydrogenated, e.g. in the presence of Raney nickel, to give sabinene hydrate.

The hydroperoxide resulting from nerol can be reduced to the corresponding hydroxyl compound and this can then be cyclized with acid catalysis to give nerol oxide.

The hydroperoxide resulting from terpinolene can be reduced to p-mentha-1,8-dien-4-ol and this can be selectively catalytically hydrogenated to give 4-terpineol.

EXAMPLE

Irradiation with Sunlight

A tubular reactor (volume 70 l) served as reactor having a closed circulation comprising a pivotable parabolic mirror channel (height 4.5 m, surface area 7.3 m$^2$, vapour-deposited aluminium on polytetrafluoroethylene, sealed on the rear side with polyester film), a glass absorber tube arranged in the focal line of the parabolic mirror channel and a supply part containing a reservoir, pump, heat exchanger, gas metering apparatus and static mixer. The parabolic mirror channel was made to track the position of the sun. The reaction solution was pumped in circulation with feed of oxygen and cooled prior to (re)entry into the absorber tube.

The mirror concentrated the solar radiation incident on the absorber tube by a factor of 20.

The reactor was situated in Spain (latitude 37.1° North).

A solution of 5.6 kg of α-thujene (GC content 85%) and 5 g of Rose Bengal in 27 kg of isopropanol was pumped in circulation in sunlight with continuous addition of oxygen. In the course of the reaction, 4 g of Rose Bengal were added in supplement. After 6 hours of reaction time the conversion rate was 99%. A solution of 5.4 kg of sodium sulphite in 29 kg of water was added, the mixture was heated to 70° C. and pumped in circulation for 3 hours.

Work-up of the reaction mixture: at atmospheric pressure, 32 kg of isopropanol/water mixture were distilled off. In order to facilitate the phase separation, 2 kg of toluene were added to the distillation bottom product. The organic phase separating out was washed with water and distilled over 0.1 kg of Na$_2$CO$_3$. 4.5 kg of 4-hydroxy-β-thujene (GC content 78%) were obtained corresponding to a yield of 65% of theory.

We claim:

1. In the oxidation of an olefinic terpene with oxygen under radiation with light, the improvement which comprises utilizing a light source such that no more than 10% of the total energy of the light emitted is apportioned to the wavelength range of 200 to 400 nm, based on the wavelength range of 200 to 700 nm radiated by the light source, the radiation being of an intensity such that the reaction achieves a conversion rate of 95% in less than 12 hours.

2. A process according to claim 1, wherein the light source is sunlight.

3. A process according to claim 1, wherein the light is an artificial light.

4. A process according to claim 3, wherein the terpene comprises at least one compound selected from the group consisting of mono- and bicyclic olefinic terpenes.

5. A process according to claim 1, wherein the terpene comprises at least one compound selected from the group consisting of myrcene, ocimene, geraniol, nerol, linalool, myrcenol, lavandulol, citronellol, limonene, α- and γ-terpinene, terpinolene, α- and β-phellandrene, α- and β-pinene, camphene, carene and α-thujene.

6. The process according to claim 1, wherein no more than 1% of the total energy of the emitted light is apportioned to the wavelength range of 200 to 300 nm, based on the wavelength range of 200 to 700 nm radiated by the light source.

7. A process according to claim 6, wherein the terpene comprises at least one compound selected from the group consisting of myrcene, ocimene, geraniol, nerol, linalool, myrcenol, lavandulol, citronellol, limonene, α- and γ-terpinene, terpinolene, α- and β-phellandrene, α- and β-pinene, camphene, carene and α-thujene.

8. A process according to claim 6, wherein the light is an artificial light.

9. A process according to claim 6, wherein the light is an artificial light and the terpene comprises at least one compound selected from the group consisting of mono- and bicyclic olefinic terpenes.

10. In the preparation of a terpenealcohol by oxidizing an olefinic terpene with oxygen under radiation with light, to produce a terpene hydroperoxide, and then reducing the hydroperoxide to the terpene alcohol, the improvement which comprises effecting the oxidation according to claim 1.

11. In the preparation of rose oxide by oxidizing citronellol with oxygen under radiation with light, to produce its hydroperoxide, reducing the hydroperoxide to 3,7-dimethyl-5-octene-1,7-diol, and ring closing the diol to rose oxide, the improvement which comprises effecting the oxidation according to claim 1.

12. In the preparation of sabinene hydrate by oxidizing α-thujene with oxygen under radiation with light, to produce its hydroperoxide and reducing the hydroperoxide to 4-hydroxy-β-thujene, and then reducing the 4-hydroxy-β-thujene to sabinene hydrate, the improvement which comprises effecting the oxidation according to claim 1.

13. In the preparation of nerol oxide by oxidizing nerol with oxygen under radiation with light, to produce its hydroperoxide, reducing the hydroperoxide to the corresponding hydroxyl compound, and then cyclizing such hydroxyl compound to nerol oxide, the improvement which comprises effecting the oxidation according to claim 1.

14. In the preparation of 4-terpineol by oxidizing terpinolene with oxygen under radiation with light, to produce terpinolene hydroperoxide, reducing the hydroperoxide to p-mentha-1,8-dien-4-ol, and reducing the p-mentha-1,8-dien-4-ol to 4-terpineol, the improvement which comprises effecting the oxidation according to claim 1.

* * * * *